(12) United States Patent
Koide et al.

(10) Patent No.: US 7,950,923 B2
(45) Date of Patent: May 31, 2011

(54) OCCLUSAL PLANE ANALYZER, ARTICULATOR, AND OCCLUSAL PLANE ANALYZING METHOD

(75) Inventors: Kaoru Koide, Niigata (JP); Iori Saitoh, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 287 days.

(21) Appl. No.: 12/230,091

(22) Filed: Aug. 22, 2008

(65) Prior Publication Data

US 2009/0053670 A1    Feb. 26, 2009

(30) Foreign Application Priority Data

Aug. 23, 2007  (JP) .................................. 2007-217122

(51) Int. Cl.
*A61C 11/00* (2006.01)
(52) U.S. Cl. ............................... 433/55; 433/56; 433/68
(58) Field of Classification Search .............. 433/53–69, 433/72–75; 600/589–590; 434/264; D24/128; 33/511–514
See application file for complete search history.

(56) References Cited

U.S. PATENT DOCUMENTS

| | | | |
|---|---|---|---|
| 1,457,385 A * | 6/1923 | Monson | 433/61 |
| 2,907,085 A * | 10/1959 | Bosland | 24/10 R |
| 2,930,127 A * | 3/1960 | Mann et al. | 433/56 |
| 5,360,337 A * | 11/1994 | Westdyk | 433/64 |
| 5,425,636 A * | 6/1995 | Ghim | 433/64 |
| 2004/0157191 A1 | 8/2004 | Nishihama | |
| 2007/0117065 A1* | 5/2007 | Nishihama | 433/167 |

FOREIGN PATENT DOCUMENTS

| | | |
|---|---|---|
| JP | 2003-190186 | 7/2003 |
| JP | 2003-245291 | 9/2003 |
| JP | 3680139 | 8/2005 |

OTHER PUBLICATIONS

"The Journal of Dental Technics Extra Issue: Illustrative Basic Knowledge of Occlusion", edited by Tadashi Imada, Ishiyaku Publishers, Inc., Jun. 30, 1984, pp. 118-121.
"The Journal of Dental Technology Extra Issue 2002: Visual Basic Knowledge of Occlusion", edited by Katsuji Fujita, Ishiyaku Publishers, Inc., Jun. 25, 2002, pp. 100-103.

* cited by examiner

*Primary Examiner* — Cris L Rodriguez
*Assistant Examiner* — Edward Moran
(74) *Attorney, Agent, or Firm* — Wenderoth, Lind & Ponack, L.L.P.

(57) ABSTRACT

An occlusal plane analyzer (5) is composed of an analysis board (7) made of a magnetic material and held above a lower jaw model (2), a magnet (8) which can attract the analysis board (7) with magnetic force and which has a circular support hole (15) going through in an attraction direction of the magnetic force, and a Monson curve imparting tool (9) composed of a spherical body section (17) which is made of a magnetic material with a diameter larger than an inside diameter of the support hole (15) and which can be attracted to the support hole (15), an extended section (18) extending from the spherical body section (17), and a spherical surface regenerating section (19) further extending from a distal end of the extended section (18) for drawing a circular arc concentric with the spherical body section (17).

7 Claims, 20 Drawing Sheets

OCCLUSAL PLANE ANALYZER, ARTICULATOR, AND OCCLUSAL PLANE ANALYZING METHOD

This application is based on application No. 2007-217122 filed in Japan, the contents of which are hereby incorporated by reference.

BACKGROUND OF THE INVENTION

The present invention relates to an occlusal plane analyzer, an articulator and an occlusal plane analyzing method used for analysis of occlusal planes and determination of occlusal planes in creating prosthetic appliances.

It is known that an occlusal plane constituted of continuous occlusal surfaces of teeth generally forms a spherical plane (Monson spherical plane) with a radius of 4 inches.

Broadrick occlusal plane analyzer is used as an occlusal plane analyzer for analyzing occlusal planes. As described in "The Journal of Dental Technics Extra Issue: Illustrative Basic Knowledge of Occlusion" edited by Takashi Imada, Ishiyaku Publishers, Inc., Jun. 30, 1984, p 118-121 and "The Journal of Dental Technics Extra Issue: Visual Basic Knowledge of Occlusion" edited by Katsuji Fujita, Ishiyaku Publishers, Inc., Jun. 25, 2002, p 102, in the Broadrick occlusal plane analyzer, first, 4-inch circular arcs from a distal angle section of a canine tooth and from a distal buccal cusp tip of a last molar or a condylar ball of an articulator are plotted with use of a compass on a flat plate held in the upper part of a lower jaw model to obtain an intersection thereof as an occlusal plane analysis point (a central point of Monson curve). Then, a 4-inch circular arc is plotted from the occlusal plane analysis point with use of the compasses on the lower jaw model, and this circular arc is used as an occlusal plane (occlusal curvature) constituted of connected tips of the buccal cusps. The Broadrick occlusal plane analyzer requires careful operation so as to prevent the fulcrum of the compass from shifting during drawing of the occlusal planes.

The occlusal plane analyzer can only show one point on the occlusal plane and it is not possible to intuitively check whether a plurality of teeth are arranged on the correct occlusal plane.

In Japanese Patent No. 3680139, JP 2003-190186 A and JP 2003-245291 A, occlusal plane analyzers are disclosed which have a rod provided above a jaw model, an arm with its one end connected to the upper end of the rod so as to be three-dimensionally rotatable, and a circular-arc nail provided on the other end of the arm, so that occlusal planes can easily be drawn with the tip of the nail. In these occlusal plane analyzers, it is necessary to adjust the fixed position of the jaw model and the position of the rod so that the rotation center of the arm on the upper end of the rod may be positioned in 4 inches from a distal angle section of a canine tooth and from a distal buccal cusp tip of a last molar of the jaw model or a condylar ball of an articulator, and this adjusting work is not easily achieved.

SUMMARY OF THE INVENTION

In view of the problem, an object of the present invention is to provide an occlusal plane analyzer, an articulator, and an occlusal plane analyzing method which allow easily drawing of an occlusal plane and which allow easily determination of an occlusal plane analysis point.

In order to accomplish the above object, the occlusal plane analyzer in the present invention includes an analysis board made of a magnetic material and held above a jaw model, a magnet which can attract the analysis board with magnetic force and which has a circular support hole going through in an attraction direction of the magnetic force, and a Monson curve imparting tool composed of a spherical body section which is made of a magnetic material with a diameter larger than an inside diameter of the support hole and which can be attracted to the support hole, an extended section extending from the spherical body section and a spherical surface regenerating section further extending from a distal end of the extended section and drawing a circular arc concentric with the spherical body section.

According to this configuration, the spherical body section is slidably rotated on the support hole of the magnet attracted to the analysis board, so that the spherical surface regenerating section of the Monson curve imparting tool is made to swing in three dimensional way and thereby an occlusal plane can be drawn. Moreover, circles having a radius of a Monson spherical plane are drawn from two reference points in the jaw model on an analysis board with use of tools such as compasses, so that the swinging center position of the Monson curve imparting tool can easily be positioned at an occlusal plane analysis point which is the center of the Monson spherical plane. Moreover, the circular-arc spherical surface regenerating section which freely swings centering around the spherical body section allows the teeth arrangement state to be checked at once.

In the occlusal plane analyzer of the invention, the analysis board may include a positioning means, which can selectively place any one of a center of a thickness of the analysis board, a center of the spherical body section attracted to the support hole when the magnet attracts a surface of the analysis board, and a center of the spherical body section attracted to the support hole when the magnet attracts a rear face of the analysis board right above the bilateral symmetry center line of the jaw model.

According to this configuration, it becomes possible to correct minute displacement of the occlusal plane analysis point due to the thickness of the spherical body section and the magnet, and to thereby draw more accurate occlusal planes.

In the occlusal plane analyzer of the invention, the extended section is preferably bent halfway.

According to this configuration, the spherical surface regenerating section can be placed over the jaw model by extending around the upper jaw model as well as the structure supporting the upper jaw model, so that occlusal planes can easily be drawn.

In the occlusal plane analyzer of the invention, the magnet preferably attracts the analysis board via the high friction sheet.

According to this configuration, the magnet is not displaced during operation of the Monson curve imparting tool.

The articulator of the invention includes the occlusal plane analysis board.

According to this configuration, occlusal plane analysis points can easily be defined and occlusal planes can easily be drawn.

An occlusal plane analyzing method of the invention includes the steps for holding an analysis board made of a magnetic material above a jaw model, plotting circular arcs on the analysis board with a predetermined radius respectively centering around two reference points on the jaw model, attracting a magnet having a circular support hole going through front and rear surfaces thereof to the analysis board so that an intersection of the two circular arcs plotted on the analysis board is aligned with a center of the support hole, attracting a spherical body section of a Monson curve imparting tool to the support hole, the Monson curve imparting tool comprising the spherical body section made of a magnetic material with a diameter larger than an inside diameter of the support hole, an extended section extending from the spherical body section and a spherical surface regenerating section further extending from a distal end of the extended section and drawing a circular arc concentric with the spherical body section, and slidably rotating the spherical body section upon the support hole so as to draw an occlusal plane on the jaw model with the spherical surface regenerating section.

According to this method, the spherical body section which serves as the swinging center of the Monson curve imparting tool is held by the magnet, so that positioning of the occlusal plane analysis point is facilitated and therefore the occluded condition of a plurality of teeth can be checked all at once with the circular-arc spherical surface regenerating section which freely swings.

In the occlusal plane analyzing method of the invention, circular arcs may be plotted on the analysis board by placing impact paper onto a board surface of the analysis board, and putting the spherical body section into pressure contact with the impact paper in a state where a reference point on the jaw model is in contact with the spherical surface regenerating section.

According to this method, the position of the occlusal plane analysis point can be determined with the Monson curve imparting tool without using compasses. In the Monson curve imparting tool, any part of the circular-arc spherical surface regenerating section may be brought into contact with a reference position of the jaw model, which facilitates operation of the analyzer.

According to the present invention, the spherical body section which serves as the swinging center of the Monson curve imparting tool is held by the magnet, so that positioning of the occlusal plane analysis point is facilitated and therefore the teeth arrangement state can be checked at once with the circular-arc spherical surface regenerating section.

BRIEF DESCRIPTION OF THE DRAWINGS

These and other objects and features of the present invention will become apparent from the following description taken in conjunction with the preferred embodiments thereof with reference to the accompanying drawings, in which.

DETAILED DESCRIPTION OF THE INVENTION

Figure 1:
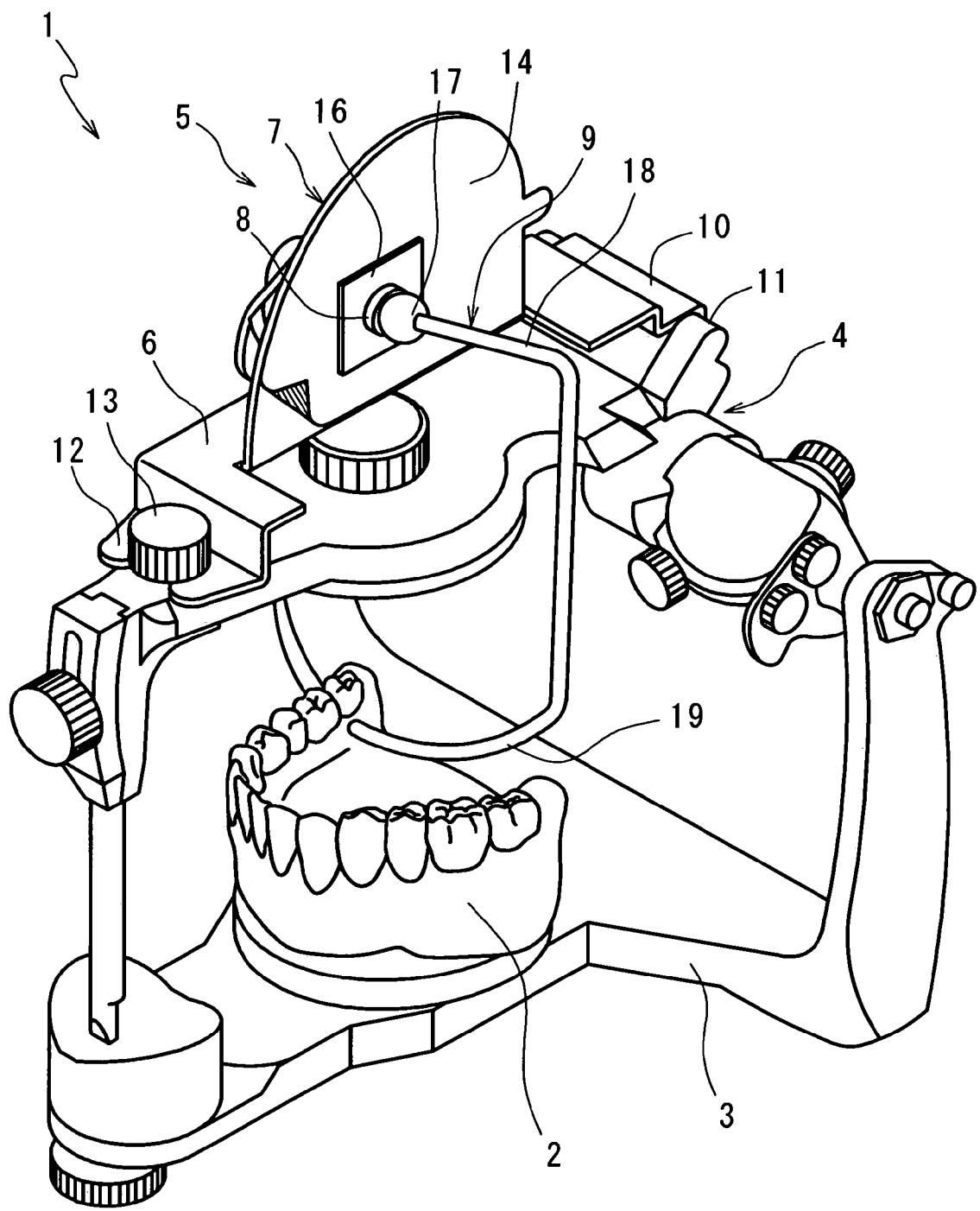
FIG. 1 is a perspective view of an articulator having an occlusal plane analyzer in a first embodiment of the invention.

FIG. 1 shows an articulator 1 as a first embodiment of the invention. The articulator 1 is composed of a lower frame 3 for holding a lower jaw model 2, an upper frame 4 capable of holding an upper jaw model (not shown), and an occlusal plane analyzer 5 for checking the occlusal plane between the lower jaw model 2 and the upper jaw model. The upper frame 4 can swing with respect to the lower frame 3 so as to reproduce motions of a jaw joint.

Figure 2:
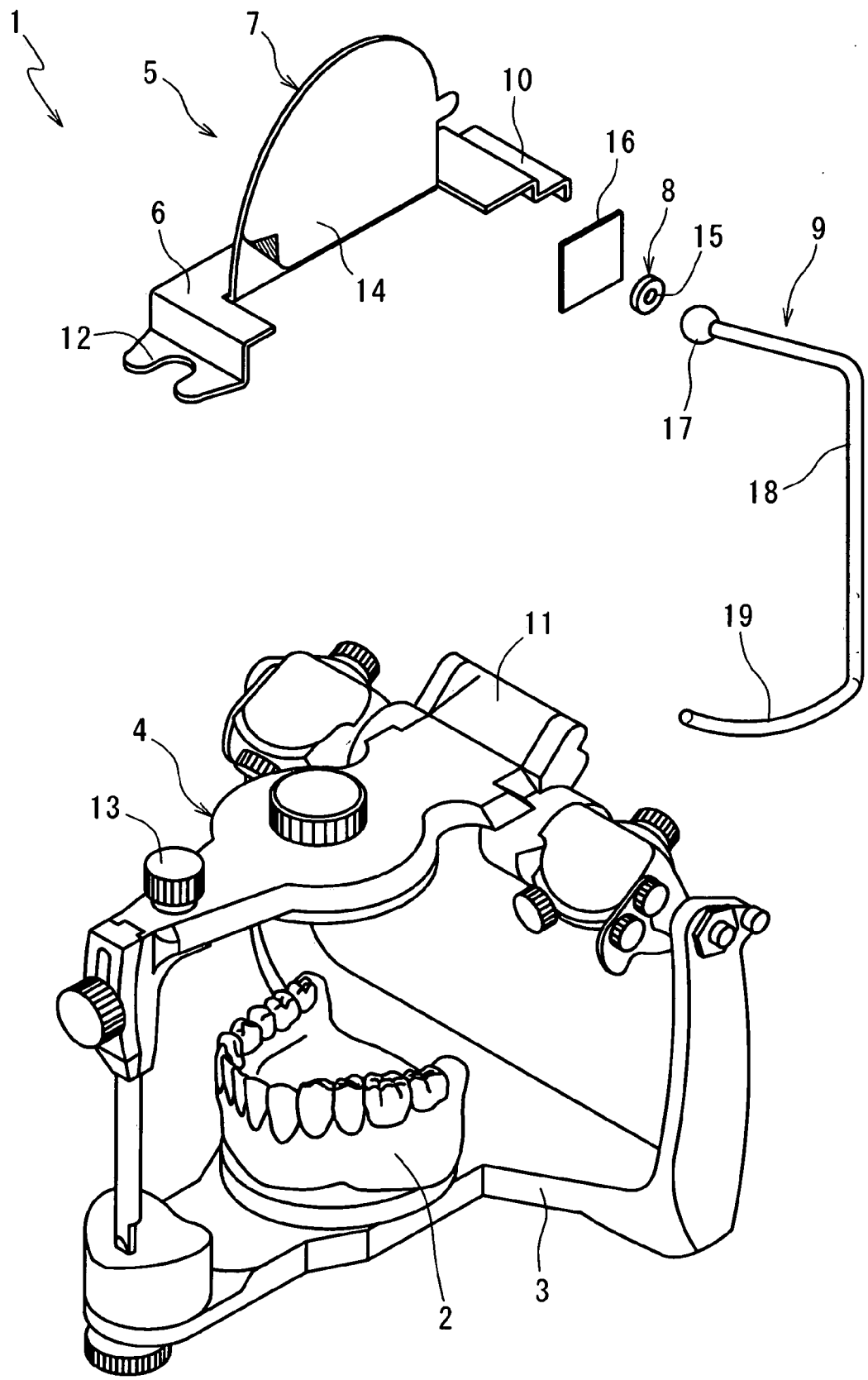
FIG. 2 is an exploded perspective view of the articulator of FIG. 1.

As shown in FIG. 2, the occlusal plane analyzer 5 is composed of an analysis board 7 made of a magnetic material, having a holding section 6 fixed on the upper frame 4, and mounted on the upper frame 4 so as to stand thereon, a magnet 8 attracting the analysis board 7 by magnetic force, and a Monson curve imparting tool 9 attracted to the magnet 8.

In the analysis board 7, a fitting section 10 at the rear end of the holding section 6 fits into a receiving section 11 at the upper rear end of the upper frame 4, and an engaging section 12 at the front end is positioned and fixed onto the upper frame 4 with a screw 13. A plotting sheet 14 is stuck on the front and rear surfaces of an effective part of the analysis board 7 which is held perpendicularly. The width of the effective surfaces of the analysis board 7 in an anteroposterior direction is formed to be 4 inches that is identical to the radius of the Monson curve.

The magnet 8 is formed into a disk shape with a circular support hole 15 passing through the center of the magnet, the circular support hole 15 having an inside diameter of, for example, 4 mm. The magnet 8 can attract the analysis board 7 by its magnetic force through the plotting sheet 14 and further through a silicon sheet 16 placed on top of the plotting sheet 14. The silicon sheet 16, which is high in friction coefficient, hinders the magnet 8 from sliding on the analysis board. The silicon sheet 16 also has transparency so that the plotting sheet 14 can be seen through the silicon sheet 16.

Figure 3:
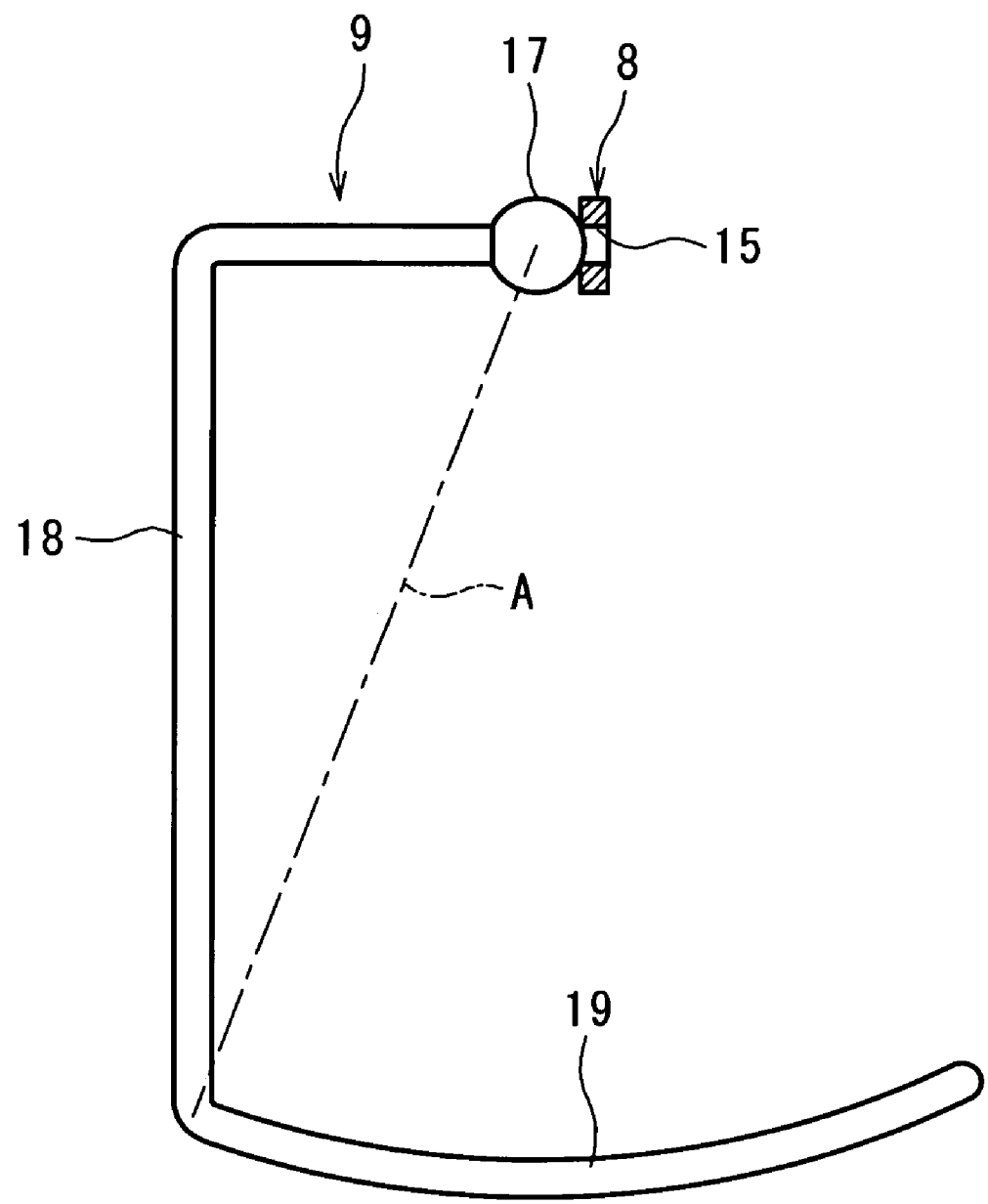
FIG. 3 is a development view of a Monson curve imparting tool in the occlusal plane analyzer of FIG. 1.

The Monson curve imparting tool 9 is made of, as shown in FIG. 3, a globular shaped spherical body section 17 which is made of a magnetic material and which can be attracted to the magnet 8, an extended section 18 linearly extending from the spherical body section 17 and bent halfway, and a spherical surface regenerating section (circular arc drawing section) 19 extending from the distal end of the extended section 18 so as to draw a circular arc concentric with the spherical body section 17.

The spherical body section 17, which has a diameter of, for example, 10 mm that is larger than the inside diameter of the support hole 15 (4 mm), comes into contact with the entire perimeter of the aperture of the support hole 15 when attracted to the magnet 8, so that the posture thereof is stabilized. If the diameter of the spherical body section 17 is too large in proportion to the support hole 15, the spherical body section 17 may roll out from the support hole 15 when torque is applied to the spherical body section 17. On the contrary, if the spherical body section 17 is small in proportion to the support hole 15, the spherical body section 17 may fail to catch enough magnetic flux of the magnet 8 and may tend to fall down due to insufficient attraction force.

The spherical surface regenerating section 19 of the Monson curve imparting tool 9 is formed so as to extend within the plane which inclines 75 degrees from the plane that the extended section 18 extends with respect to a straight line A connecting between the center of the spherical body section 17 and the distal end of the extended section 18 (see FIG. 3).

Figure 4:
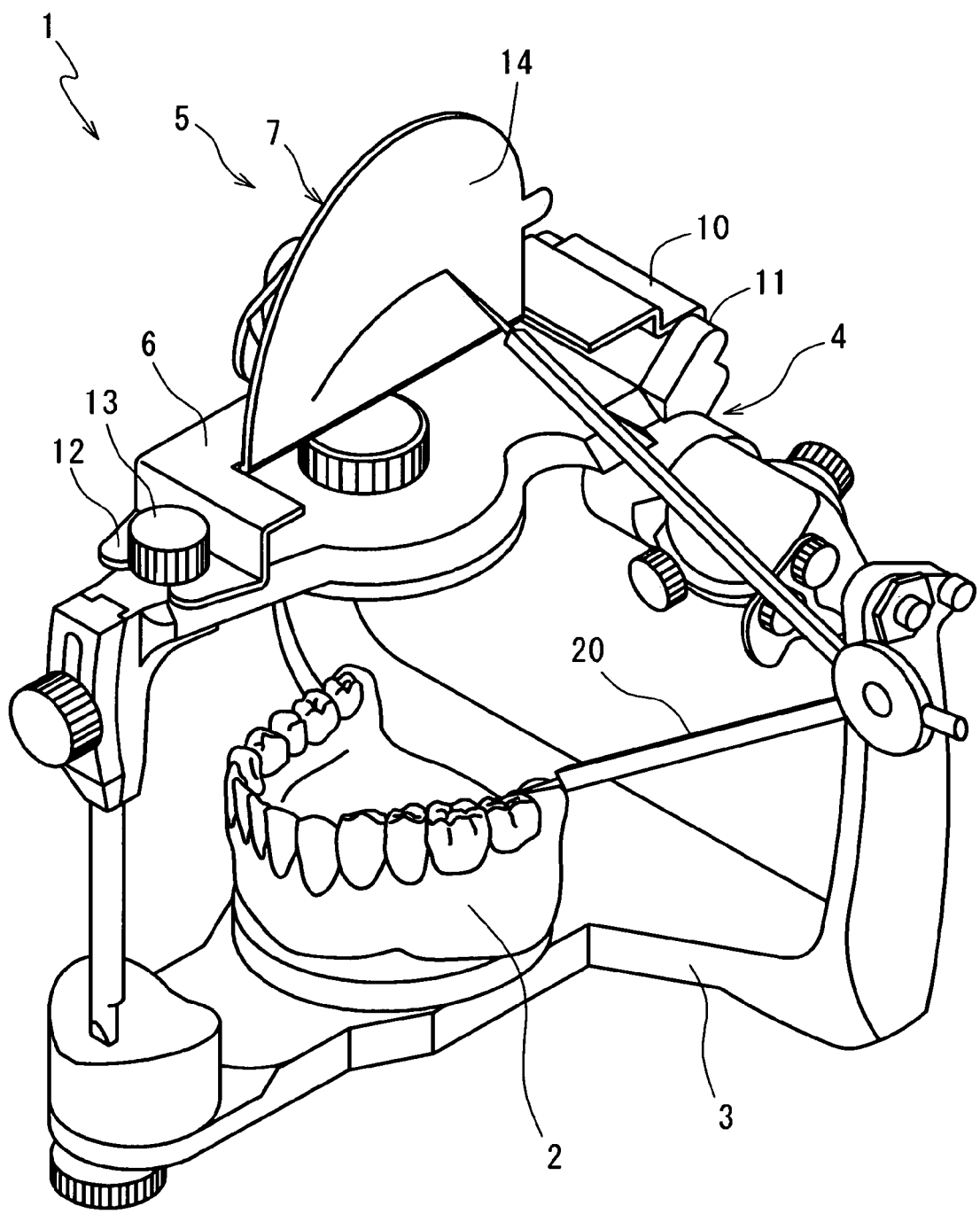
FIG. 4 is a perspective view showing the first step in use of the occlusal plane analyzer of FIG. 1.

Description is now given of how to use the occlusal plane analyzer 5 in the articulator 1. First, as shown in FIG. 4, a needle of compass 20 is brought into contact with a distal buccal cusp tip of a last molar in the lower jaw model 2, and the compass 20 is swung in this state so that a circular arc of 4 inches in radius centering around the distal buccal cusp tip of the last molar in the lower jaw model 2 is drawn on the plotting sheet 14. In this case, the compass 20 is opened in accordance with the width of the analysis board 7, so that the width of the compass 20 can be adjusted to be 4 inches which is a radius of the Monson curve.

Figure 5:
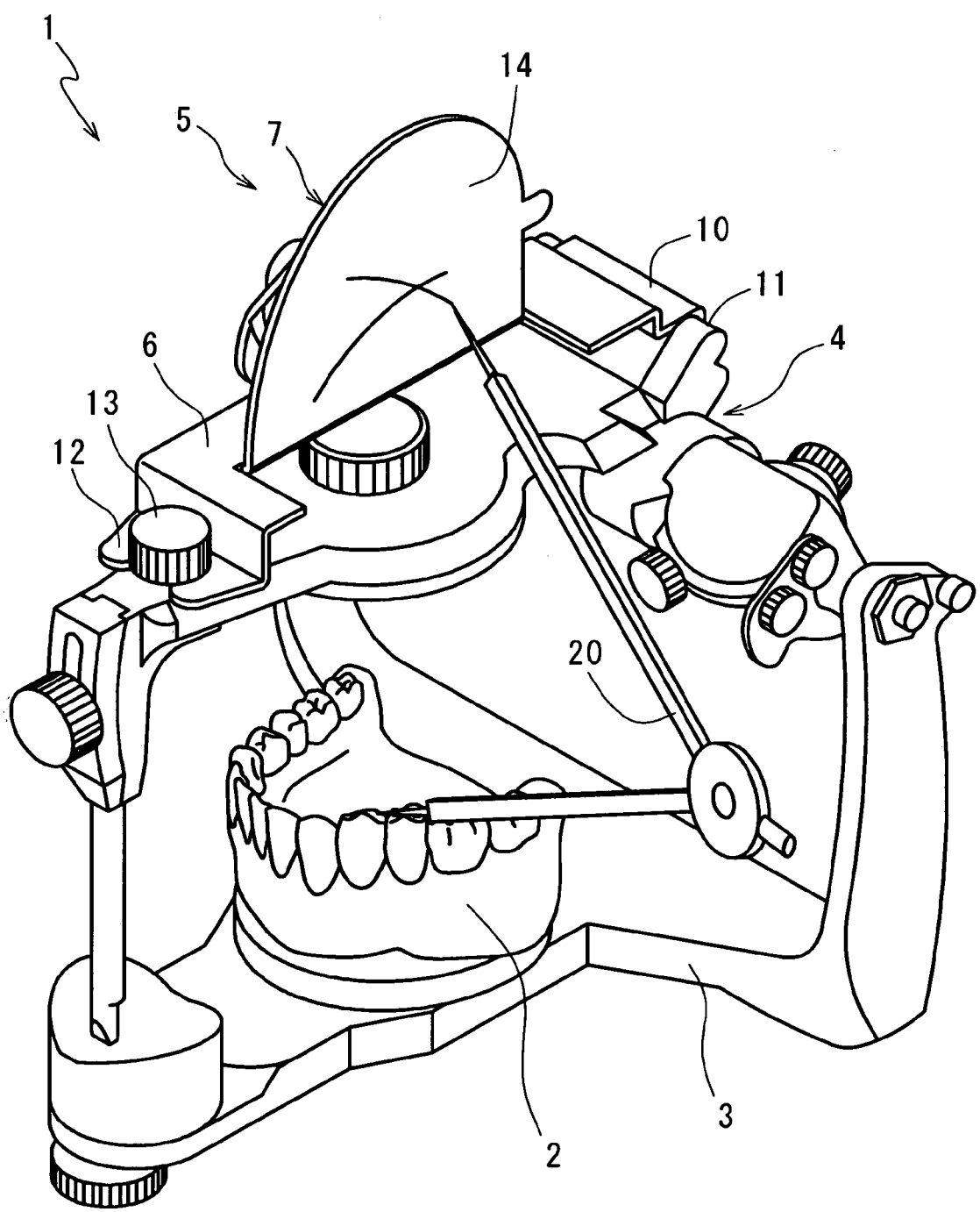
FIG. 5 is a perspective view showing the second step in use of the occlusal plane analyzer of FIG. 1.

Next, as shown in FIG. 5, the needle of the compass 20 is brought into contact with the distal angle section of a canine tooth in the lower jaw model 2, and a circular arc of 4 inches in radius centering around the distal angle section of the canine tooth is drawn on the plotting sheet 14. The intersection of the two circular arcs drawn in this way makes an occlusal plane analysis point which is the center of the occlusal plane of the lower jaw model 2.

Figure 6:
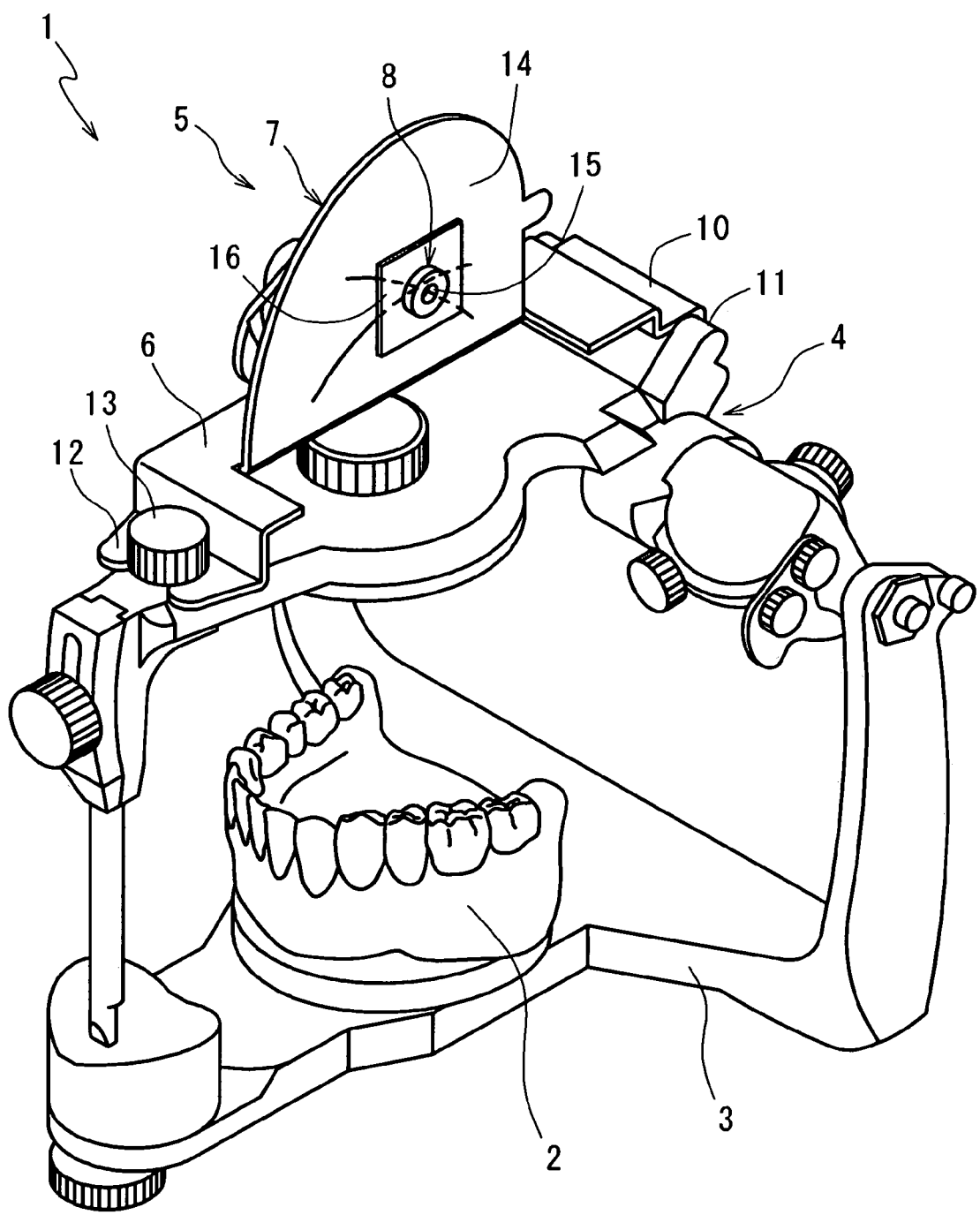
FIG. 6 is a perspective view showing the third step in use of the occlusal plane analyzer of FIG. 1.

After the two circular arcs which cross each other are drawn in this way, a user looks into the support hole 15 and makes the magnet 8 attract the analysis board 7 via the silicon sheet 16 so that the intersection of the two circular arcs drawn on the plotting sheet 14 may be positioned at the center of the support hole 15 as shown in FIG. 6.

Figure 7:
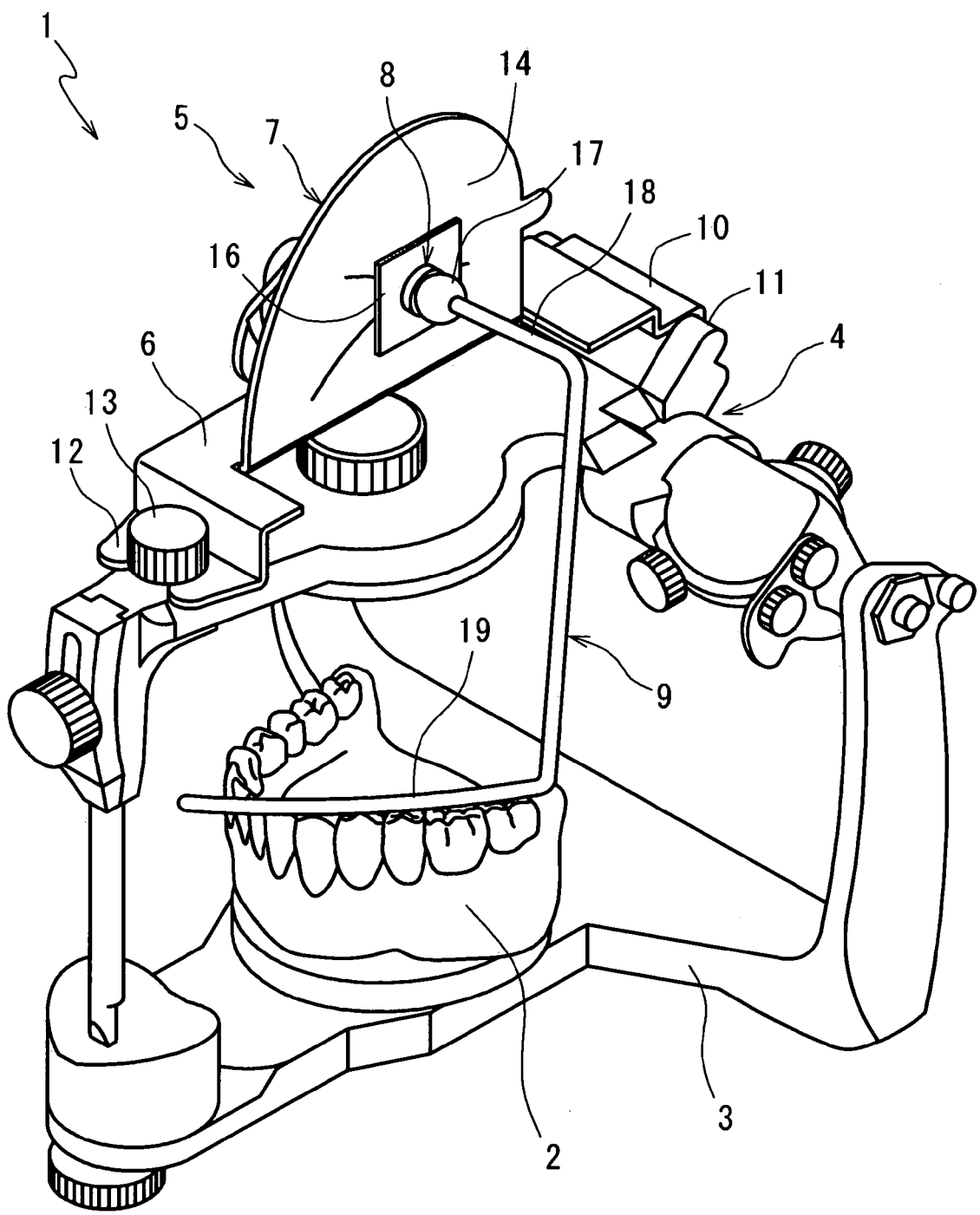
FIG. 7 is a perspective view showing the fourth step in use of the occlusal plane analyzer of FIG. 1.

Then, as shown in FIG. 7, the spherical body section 17 of the Monson curve imparting tool 9 is attracted to the support hole 15 of the magnet 8. Since the extended section 18 is bent, this makes it possible to get around the upper frame 4 (and the upper jaw model) of the articulator 1, and to place the spherical surface regenerating section 19 on the lower jaw model 2 mounted on the lower frame.

Upon application of force to the extended section or the spherical surface regenerating section 19 of the Monson curve imparting tool 9, the spherical body section 17, in the state of being attracted by the magnetic force to the magnet 8, slidably rotates on the support hole 15 while keeping the center position, by which the extended section 18 and the spherical surface regenerating section 19 are swung and axially rotated in three dimensional way. Accordingly, the occlusal plane analyzer 5 can show the occlusal plane, which is a spherical surface with a radius of 4 inches centered around an occlusal plane analysis point, on the lower jaw model 2 not only with the distal end of the spherical surface regenerating section 19 but also with any part thereof.

Figure 8:
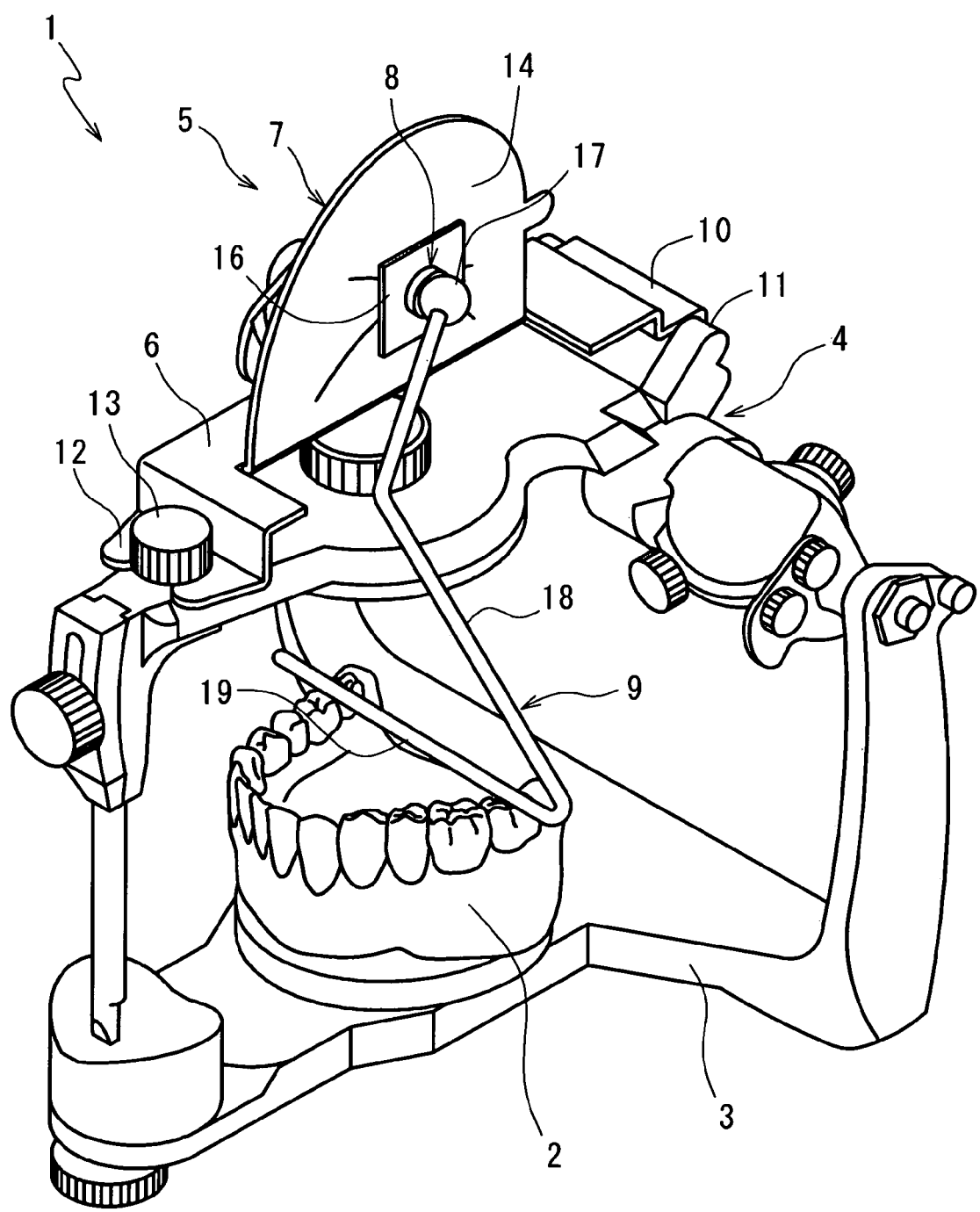
FIG. 8 is a perspective view showing an available location of the Monson curve imparting tool in the occlusal plane analyzer of FIG. 1.

Moreover, the Monson curve imparting tool 9 may freely be swung and rotated so that the spherical surface regenerating section 19 is placed along a part of the row of teeth as shown in FIG. 7 or the spherical surface regenerating section 19 is placed horizontally crossing the row of teeth as shown in FIG. 8. In short, with use of the occlusal plane analyzer 5, it becomes possible to check whether a plurality of teeth are arranged on the occlusal plane at the same time.

Thus, with use of the articulator 1 according to the invention, analysis of occlusal planes and determination of occlusal planes in creating prosthetic appliances may be performed easily and accurately.

Figure 9:
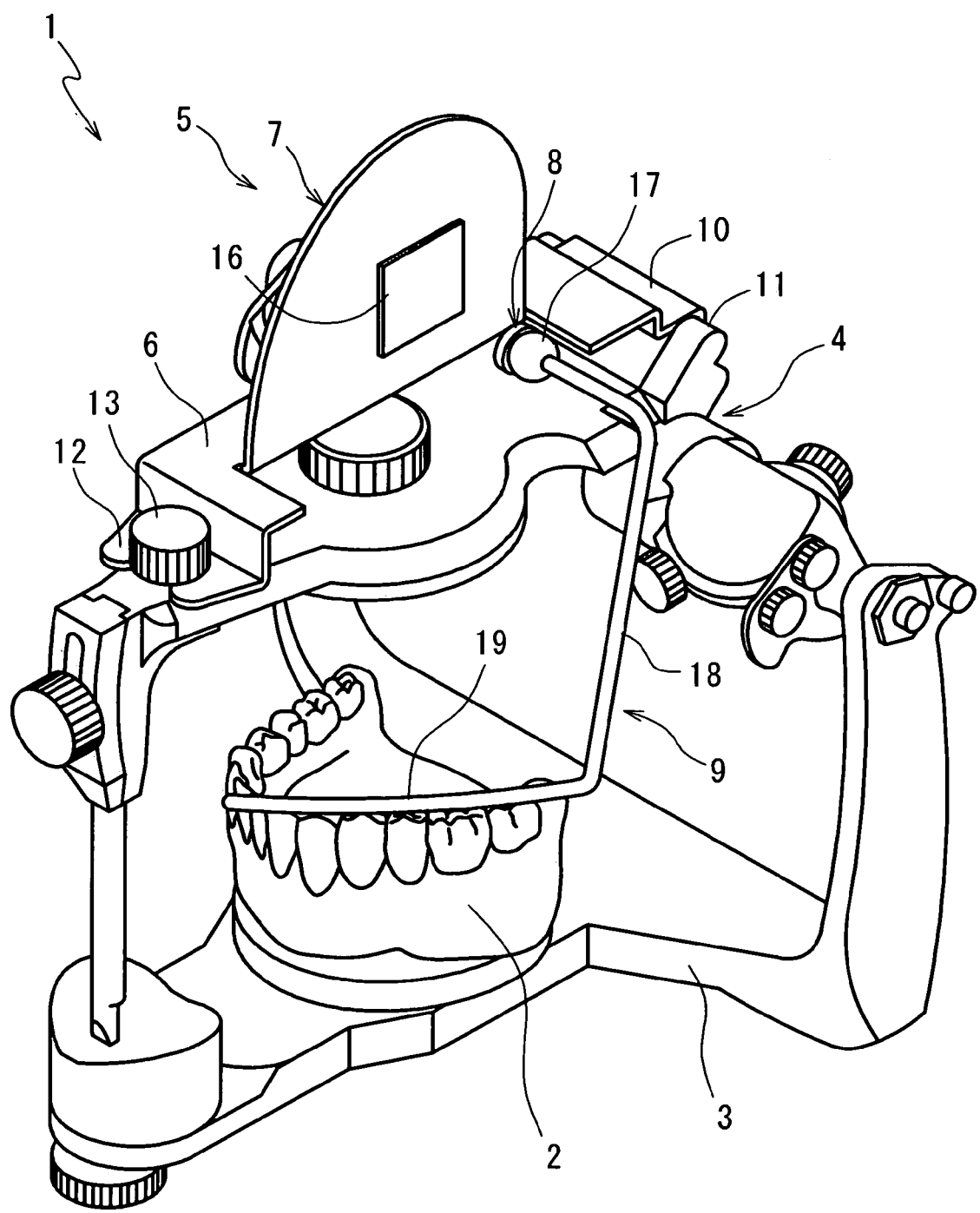
FIG. 9 is a perspective view showing the first step in simplified use of the occlusal plane analyzer of FIG. 1.
Figure 10:
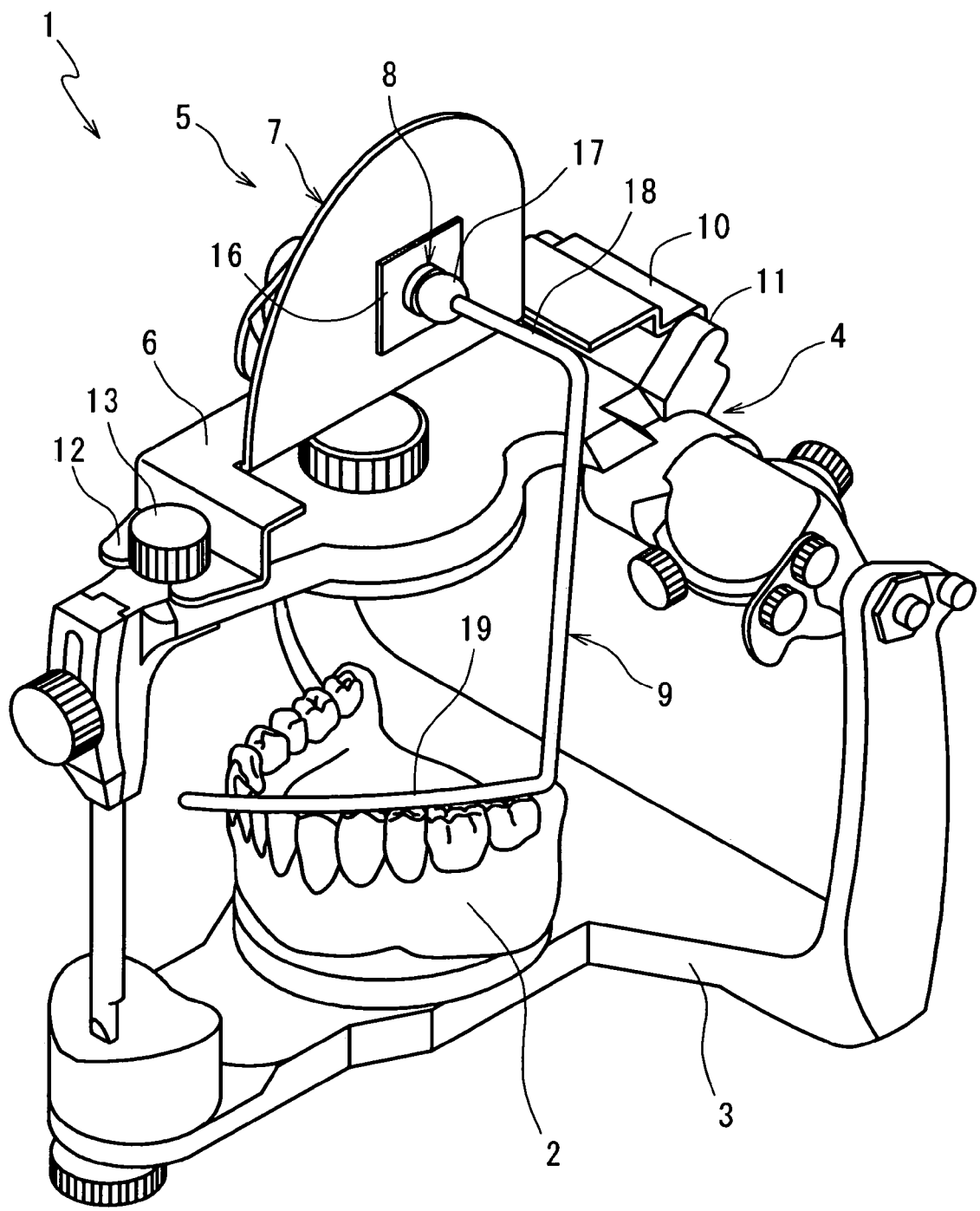
FIG. 10 is a perspective view showing the second step in simplified use of the occlusal plane analyzer of FIG. 1.

Moreover, in the articulator 1 as shown in FIG. 9, in the state where the magnet 8 attracts the spherical body section 17 of the Monson curve imparting tool 9 and where the spherical surface regenerating section 19 is in contact with the distal angle section of the canine tooth and the distal buccal cusp tip of the last molar, the Monson curve imparting tool 9 is swung centering around the distal angle section of the canine tooth and the distal buccal cusp tip of the last molar, so that the magnet 8 attracted to the spherical body section 17 may be brought into contact with the analysis board 7 and the magnet 8 can attract the analysis board 7 as shown in FIG. 10.

Thus, without drawing a circular arc on the plotting sheet 14 using the compass 20, the articulator 1 can define an occlusal plane analysis point more easily and also allows the analysis board 7 to hold the spherical body section 17 of the Monson curve imparting tool 9 with the magnet 8. According to this method, the plotting paper 14 is not necessary, though it is necessary to pay attention so as to prevent the magnet 8 from being displaced during operation of the Monson curve imparting tool 9.

Figure 11:
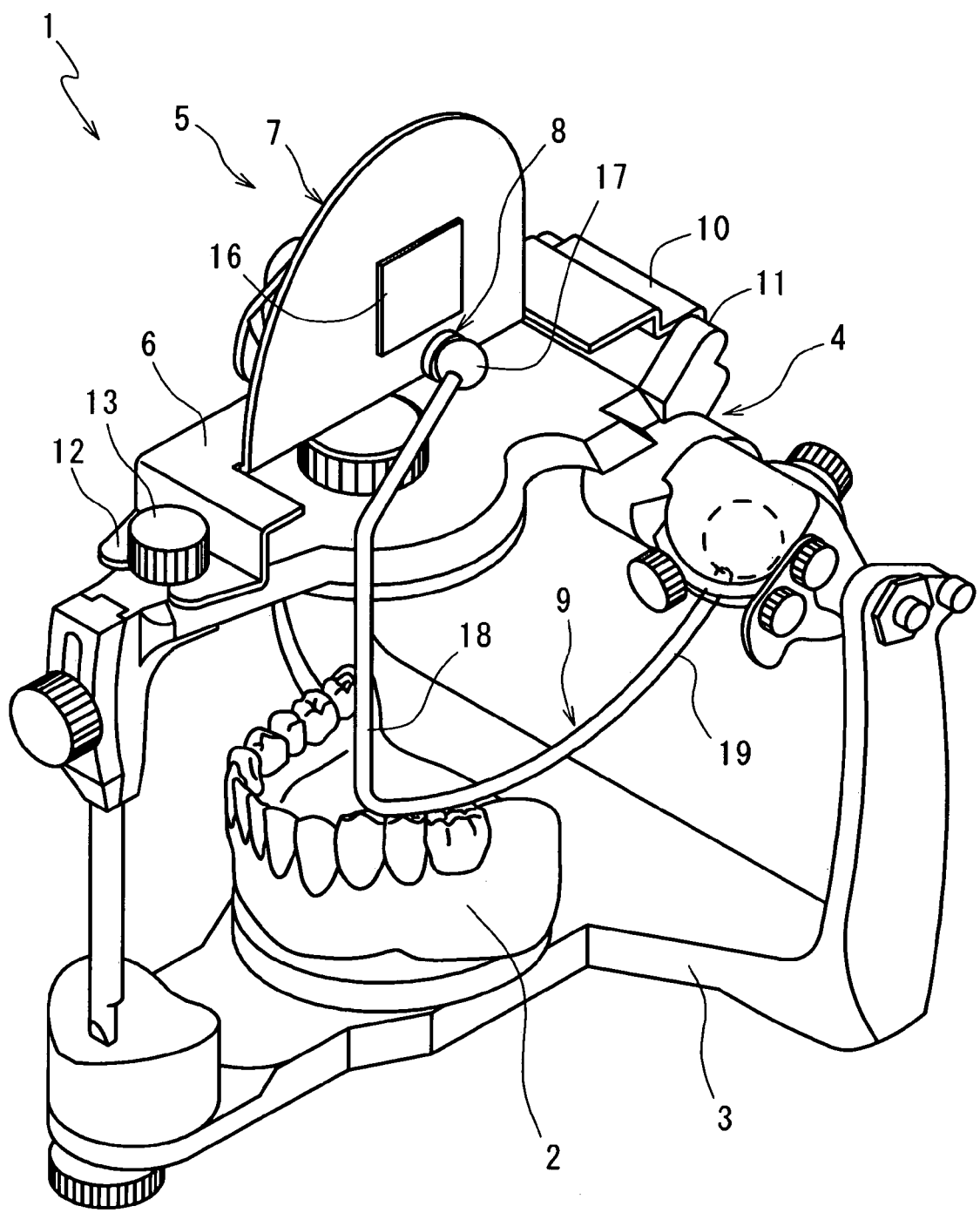
FIG. 11 is a perspective view showing an alternative to the first step in simplified use of the occlusal plane analyzer of FIG. 9.

Moreover, as shown in FIG. 11, in the case where the last molar of the lower jaw model 2 is missing, the spherical surface regenerating section 19 of the Monson curve imparting tool 9 may be put in contact with the distal angle section of the canine tooth, and also the distal end may be put in contact with a condylar ball (a sphere serving as the swinging center of the lower frame 3 and the upper frame 4) of the articulator 1, so that the spherical body section 17 is positioned on the analysis board 7 and is held by the magnet 8.

Figure 12:
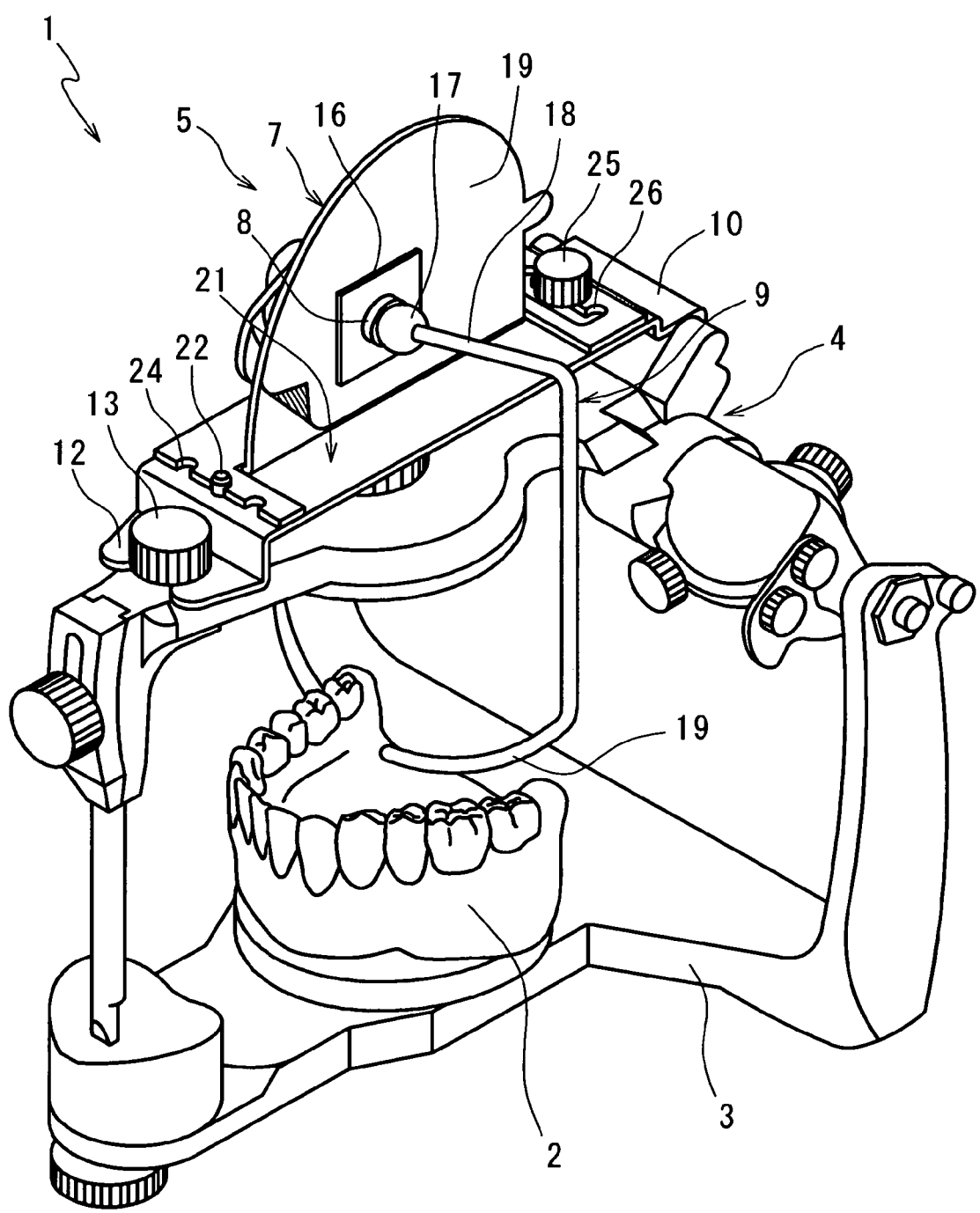
FIG. 12 is a perspective view of an articulator in a second embodiment of the invention.
Figure 13:
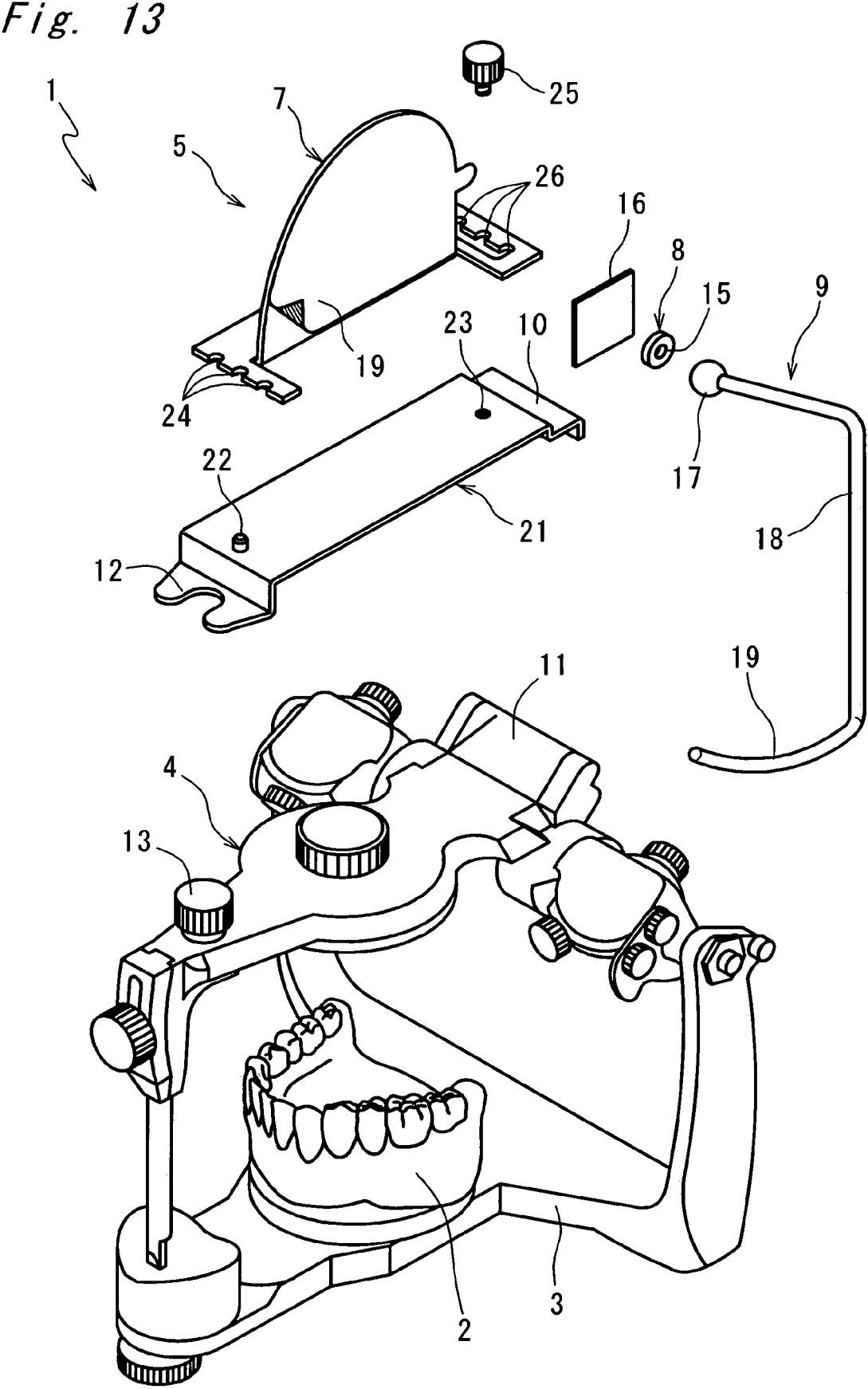
FIG. 13 is an exploded perspective view of the articulator of FIG. 12.

Further, an articulator 1 in a second embodiment of the invention is shown in FIG. 12 and FIG. 13. In the following description, like component members are designated by like reference numerals to omit redundant explanation.

The occlusal plane analyzer 5 of the articulator 1 in the present embodiment has a retainer plate 21 fixed onto the upper frame 4, so that the analysis board 7 is mounted on the retainer plate 21. The retainer plate 21 has a centering pin 22 projecting upward and a tapped hole 23.

The analysis board 7 has three front slits 24 which can engage with the centering pin 22, and three rear slits 26 which can engage with a screw 25 screwed in the tapped hole 23 and which are connected to each other, by which the analysis board 7 can be fixed at three different positions in the transverse direction on the retainer plate 21.

Three positions to fix the analysis board 7 onto the retainer plate 21 with the front slits 16 and the rear slits 18 are constituted of a position at which the center of the thickness of the analysis board 7 is retained right above the bilateral symmetry center line of the articulator 1, i.e., the lower jaw model 2 held on the lower frame 3, a position at which the center of the spherical body section 17 when the Monson curve imparting tool 9 is held by the magnet 8 on the front surface of the holding section 7 is retained right above the bilateral symmetry center line of the lower jaw model 2, and a position at which the center of the spherical body section 17 when the Monson curve imparting tool 9 is held by the magnet 8 on the rear surface of the holding section 7 is retained right above the bilateral symmetry center line of the lower jaw model 2.

Figure 14:
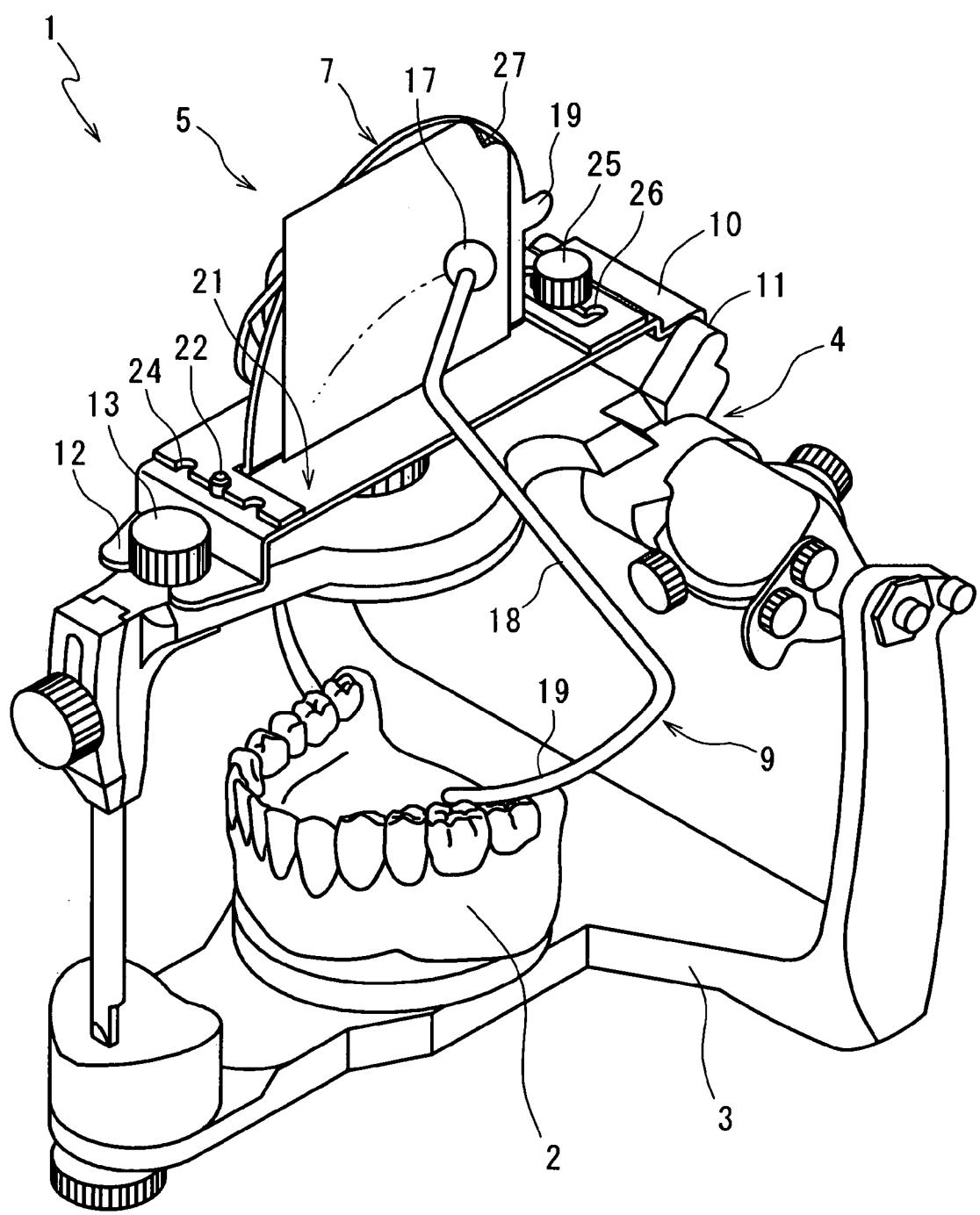
FIG. 14 is a perspective view showing the first step in use of the occlusal plane analyzer of FIG. 12.

In the present embodiment, first, as shown in FIG. 14, the analysis board 7 is mounted on the retainer plate 21 so that the center of the thickness of the analysis board 7 is positioned on the center line of the articulator 1. Carbonic paper (impact paper) 27 is further applied on top of the plotting sheet 14 of the analysis board 7 and is held thereon. Then, the distal buccal cusp tip of the last molar of the lower jaw model 2 is brought into contact with the spherical surface regenerating section 19 of the Monson curve imparting tool 9, and the spherical body section 17 is pressed to the analysis board 7 so as to hold the carbonic paper 25 therebetween. Further, the Monson curve imparting tool 9 is swung by using the distal buccal cusp tip of the last molar of the lower jaw model 2 as a fulcrum, and the carbonic paper 27 is pressed to the analysis board 7 so that a circular arc may be drawn with the spherical body section 17.

Figure 15:
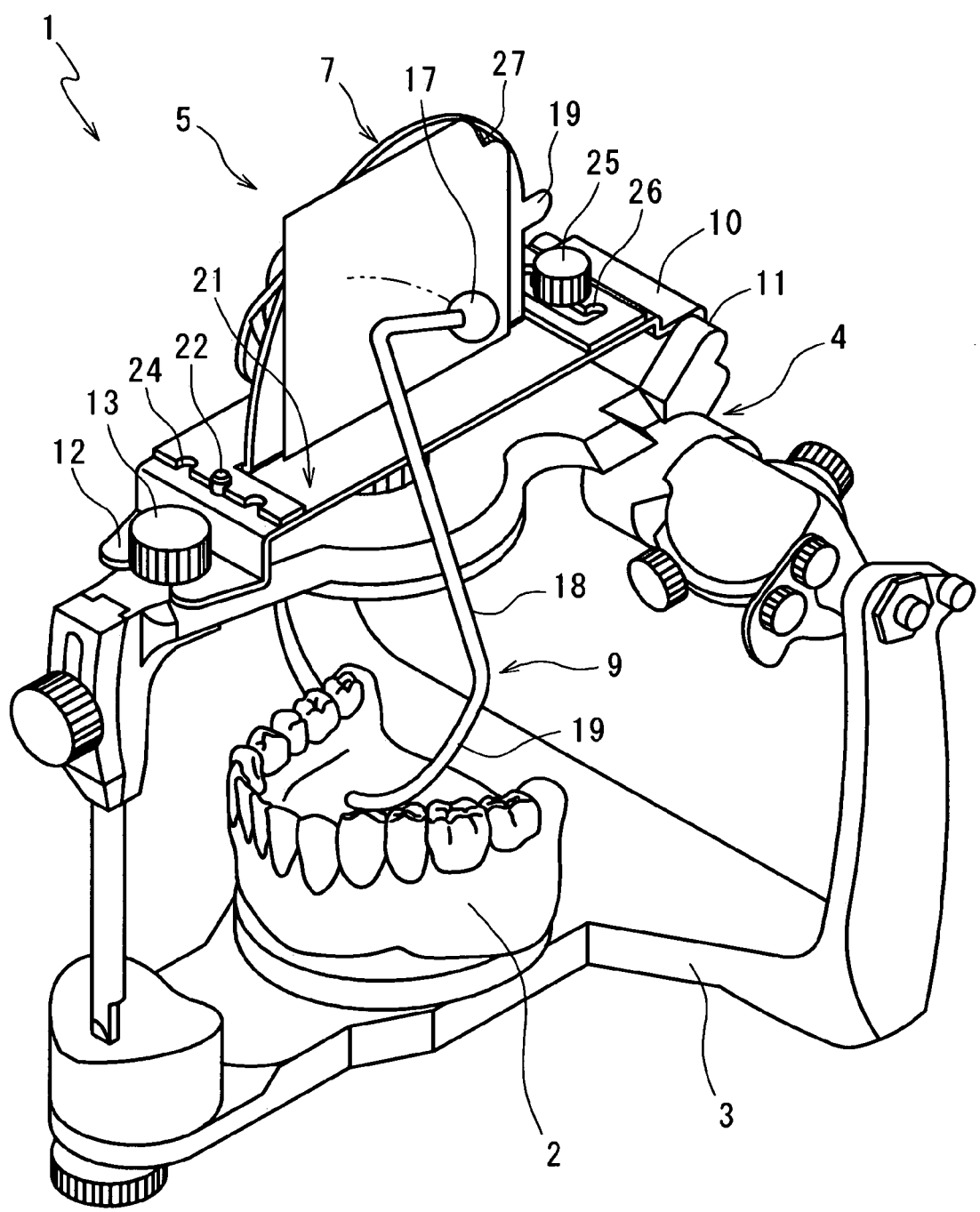
FIG. 15 is a perspective view showing the second step in use of the occlusal plane analyzer of FIG. 12.

Next, as shown in FIG. 15, in the state where the spherical surface regenerating section 19 of the Monson curve imparting tool is in contact with the distal angle section of the canine tooth of the lower jaw model 2, the Monson curve imparting tool 9 is swung and the carbonic paper 27 is pressed to the analysis board 7 so that a circular arc may be drawn with the spherical body section 17.

Figure 16:
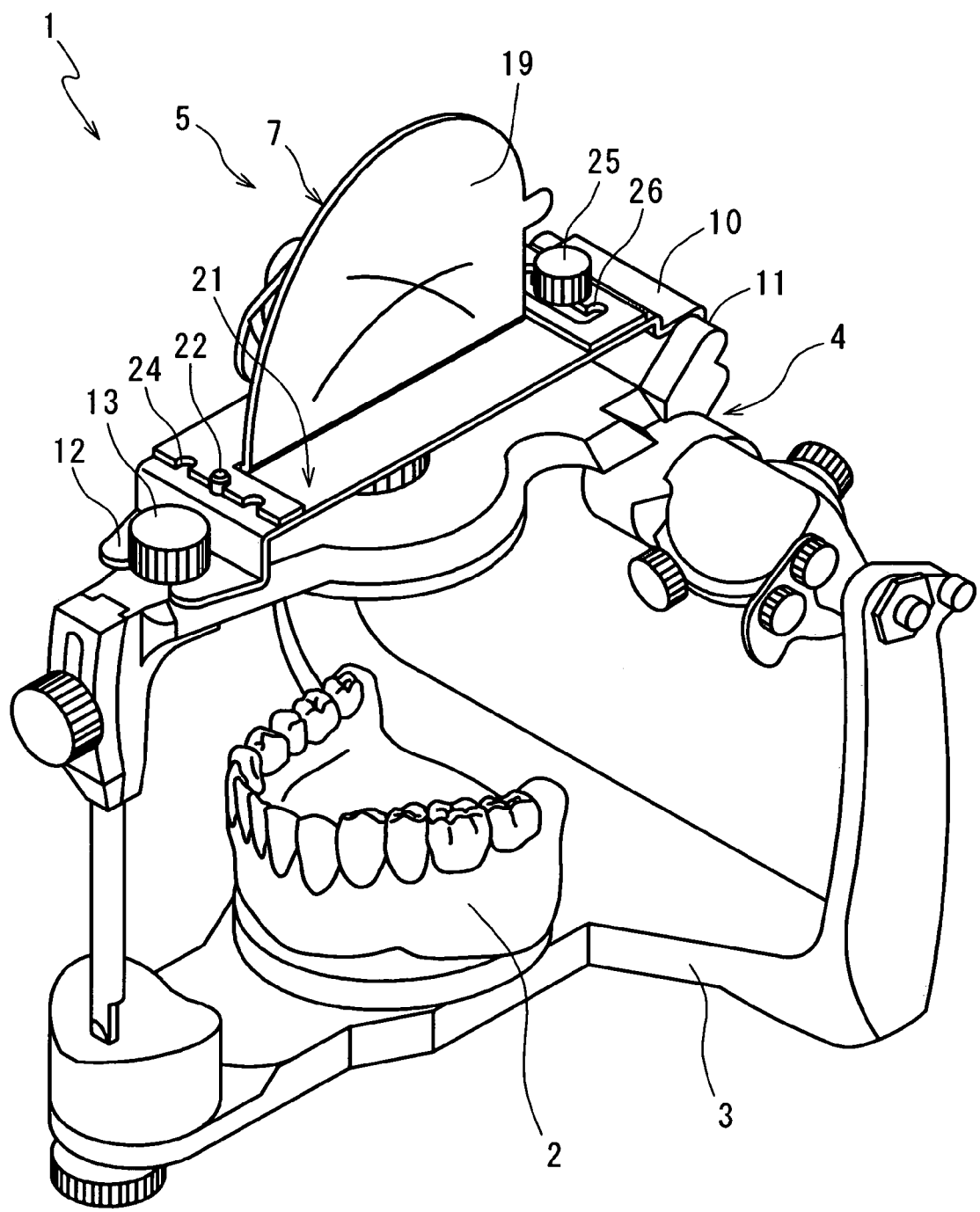
FIG. 16 is a perspective view showing the third step in use of the occlusal plane analyzer of FIG. 12.

As the carbonic paper 25 is removed, two circular arcs are drawn on the plotting sheet 14 as shown in FIG. 16. The two circular arcs present an occlusal plane analysis point which is the center of the occlusal plane of the lower jaw model 2.

Figure 17:
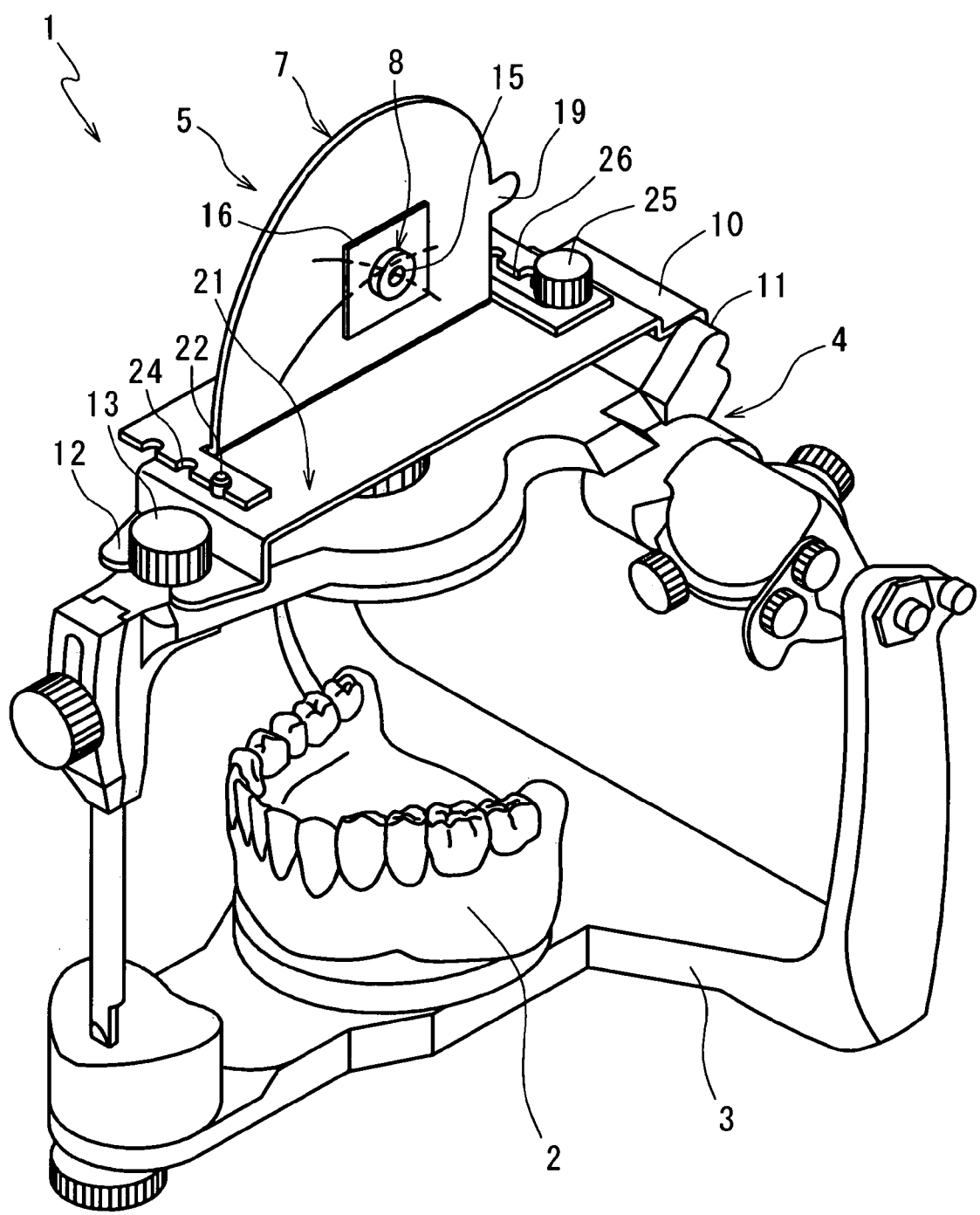
FIG. 17 is a perspective view showing the fourth step in use of the occlusal plane analyzer of FIG. 12.

Thus, once the two circular arcs crossing each other are drawn, the holding position of the analysis board 7 is changed so that the analysis board 7 is shifted to the position where the other surface of the analysis board 7 opposite to the surface carrying the circular arcs is placed as shown in FIG. 17. Then, the user looks into the support hole 15 and makes the magnet 8 attract the analysis board 7 via the silicon sheet 16 so that the intersection of the two circular arcs drawn on the plotting sheet 14 may be positioned at the center of the support hole 15.

Figure 18:
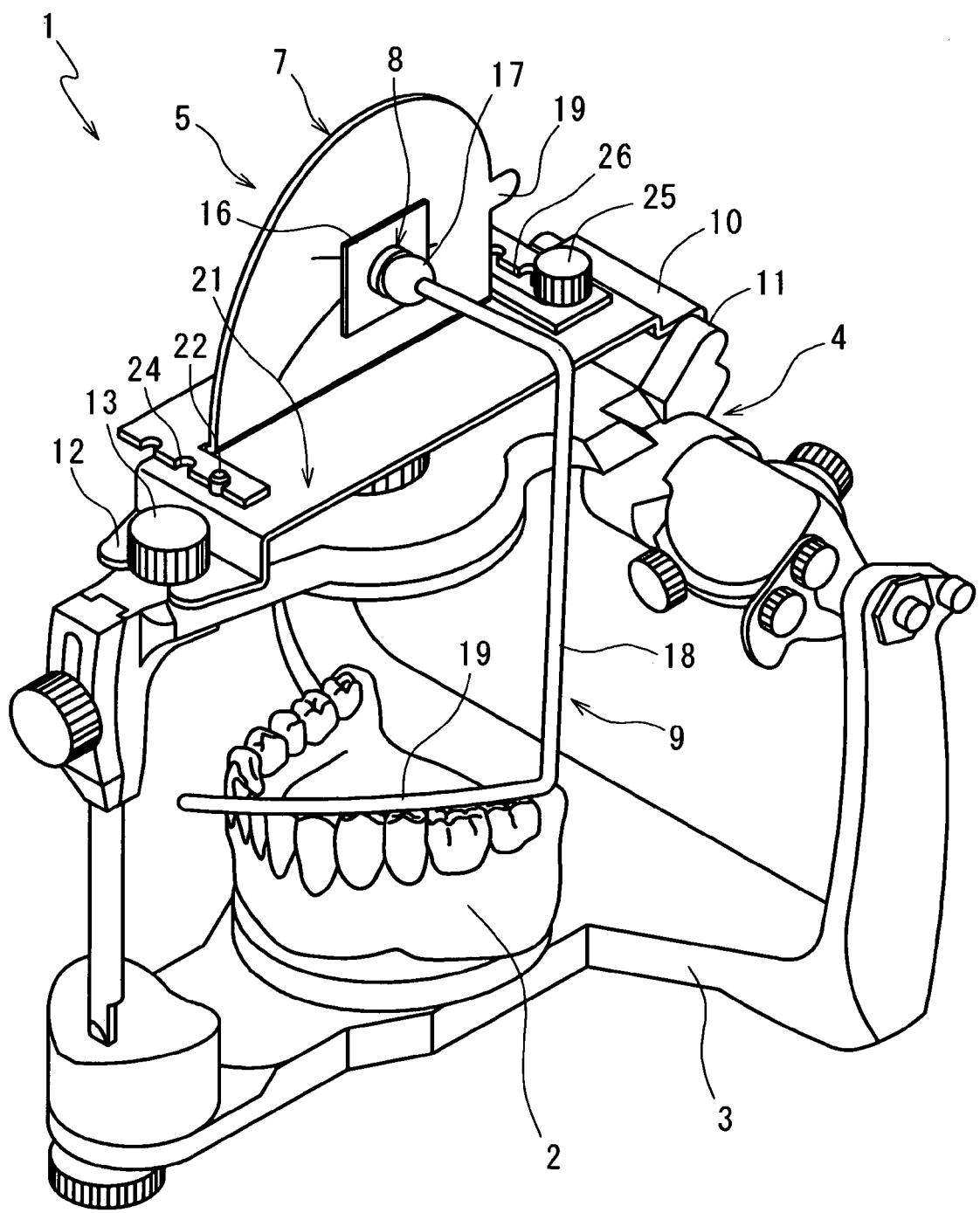
FIG. 18 is a perspective view showing the fifth step in use of the occlusal plane analyzer of FIG. 12.

Then, as shown in FIG. 18, the spherical body section 17 of the Monson curve imparting tool 9 is attracted to the support hole 15 of the magnet 8. Consequently, the extended section 18 and the spherical surface regenerating section 19 can be swung in three dimensional manner and thereby the spherical surface regenerating section 19 can present an occlusal plane on the lower jaw model 2, so that it becomes possible to correct minute displacement of the occlusal plane analysis point due to the thickness of the spherical body section and the magnet, and to thereby draw more accurate occlusal planes.

Figure 19:
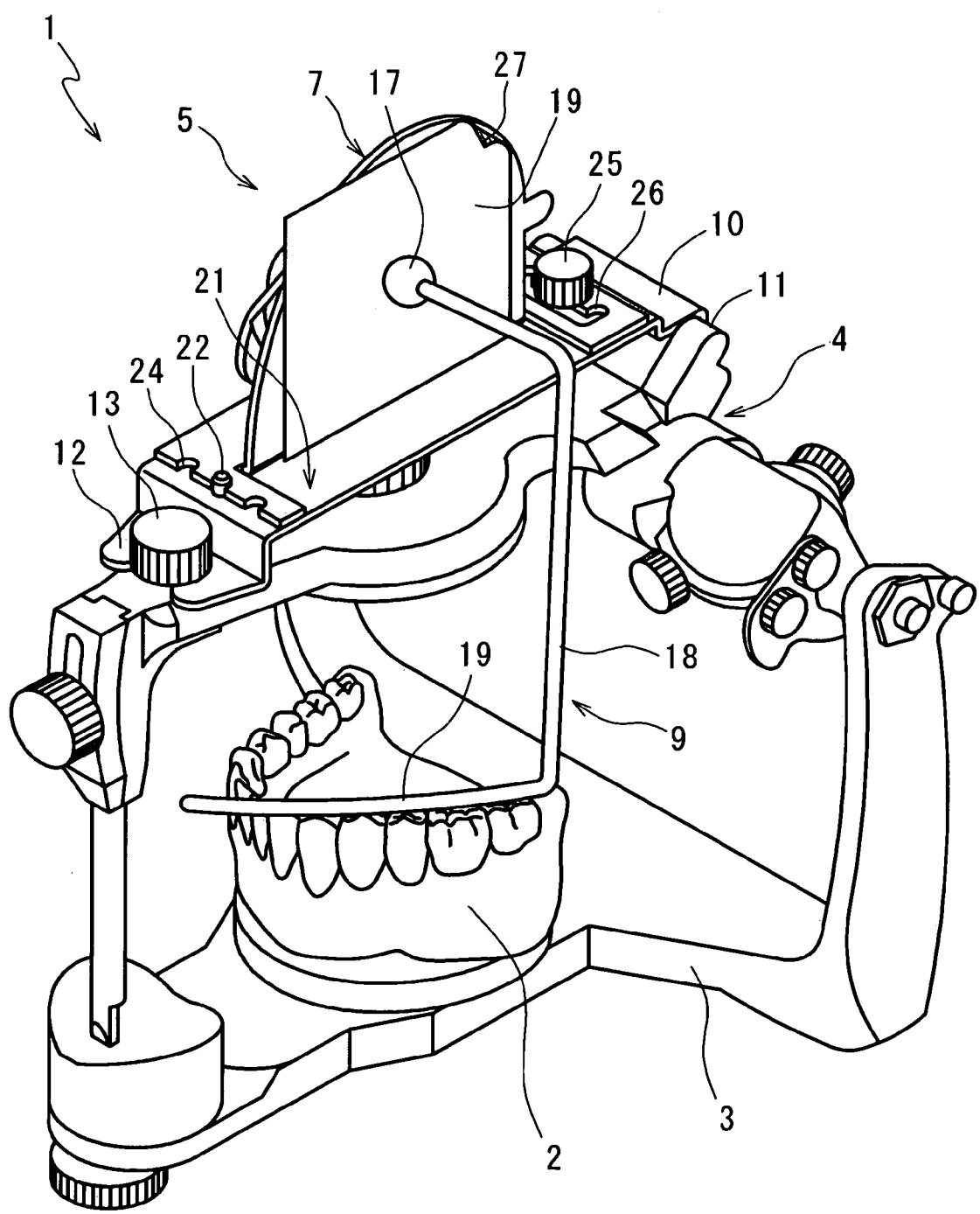
FIG. 19 is a perspective view showing the first step in simplified use of the occlusal plane analyzer of FIG. 12.
Figure 20:
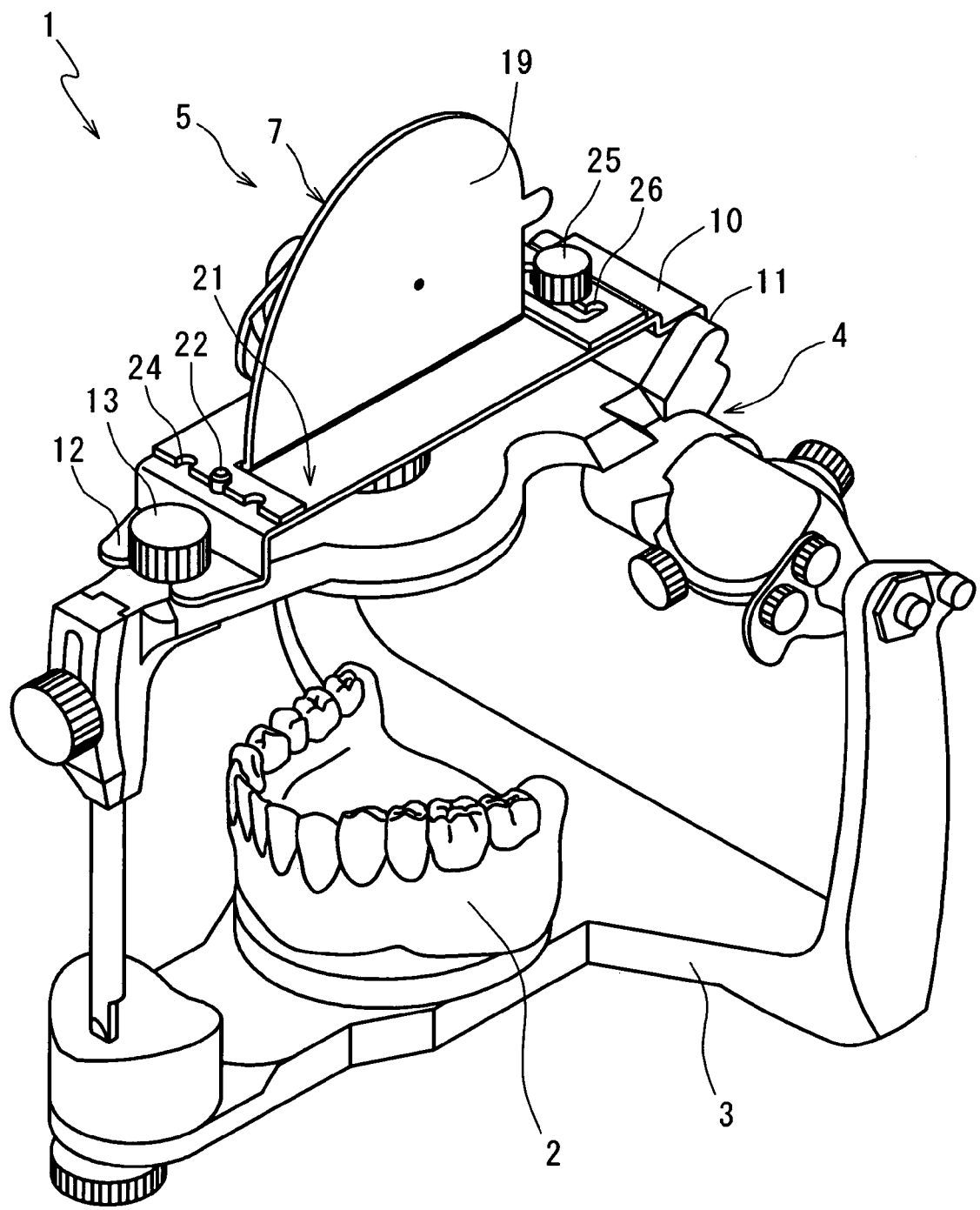
FIG. 20 is a perspective view showing the second step in simplified use of the occlusal plane analyzer of FIG. 12.

Moreover in the articulator 1 of the present embodiment, in the state where the carbonic paper 27 is applied on top of the plotting sheet 14 stuck to the analysis board 7 and is held thereon, and where the spherical surface regenerating section 19 of the Monson curve imparting tool 9 is put in contact with the distal angle section of the canine tooth and the distal buccal cusp tip of the last molar (or the condylar ball of the articulator 1) as shown in FIG. 19, the Monson curve imparting tool 9 is swung centering around the distal angle section of the canine tooth and the distal buccal cusp tip of the last molar, and the spherical body section 17 is pressed to the analysis board 7, so that as shown in FIG. 20, a point representing an occlusal plane analysis point can be plotted on the analysis board 7.

Thus, with use of the articulator 1 according to the invention, analysis of occlusal planes and determination of occlusal planes in creating prosthetic appliances may be performed easily and accurately.

Although the present invention has been fully described in connection with the preferred embodiment thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. An articulator including an occlusal plane analyzer, the occlusal plane analyzer comprising:
    an analysis board made of a magnetic material and held above a jaw model;
    a magnet which can attract with magnetic force to the analysis board and which has a circular support hole going through in an attraction direction of the magnetic force; and
    a Monson curve imparting tool comprising a spherical body section, an extended section extending from the spherical body section, and a circular arc drawing section, extending from a distal end of the extended section, for drawing a circular arc concentric with the spherical body section,
    wherein the spherical body section has a diameter that is larger than an inside diameter of the support hole and is made of a magnetic material so that the spherical body section can be attracted to the support hole by magnetic force.

2. The articulator according to claim 1, wherein the analysis board comprises:
    a plurality of slits that are engagable with a pin or a screw screwed in a tapped hole for selectively positioning any one of (i) a center of a thickness of the analysis board, (ii) a center of the spherical body section which is attracted to the support hole when the magnet attracts a surface of the analysis board, and (iii) a center of the spherical body section which is attracted to the support hole when the magnet attracts a rear face of the analysis board directly above a bilateral symmetry center line of the jaw model.

3. The occlusal plane analyzer according to claim 1, wherein the extended section includes a first portion that extends linearly from the spherical body section and a second section that extends at an angle relative to the first portion.

4. The occlusal plane analyzer according to claim 1, wherein the magnet attracts the analysis board via a high friction sheet.

5. An occlusal plane analyzing method, comprising:
    providing an articulator including an occlusal plane analyzer having an analysis board made of a magnetic material, a magnet which can attract with magnetic force to the analysis board and which has a circular support hole going through in an attraction direction of the magnetic force; and a Monson curve imparting tool comprising a spherical body section, an extended section extending from the spherical body section, and a circular arc drawing section, extending from a distal end of the extended section, for drawing a circular arc concentric with the spherical body section, wherein the spherical body section has a diameter that is larger than an inside diameter of the support hole and is made of a magnetic material so that the spherical body section can be attracted to the support hole by magnetic force;
    holding the analysis board above a jaw model;
    plotting circular arcs on the analysis board with a predetermined radius respectively centering around two reference points on the jaw model;

attracting the magnet via the circular support hole, which goes through front and rear surfaces thereof, to the analysis board so that an intersection of the two circular arcs plotted on the analysis board is aligned with a center of the support hole;

attracting a spherical body section of the Monson curve imparting tool to the support hole and drawing a circular arc concentric with the spherical body section; and slidably rotating the spherical body section upon the support hole so as to draw an occlusal plane on the jaw model with the circular arc drawing section.

6. The occlusal plane analyzing method according to claim 5, wherein the circular arcs are plotted on the analysis board by placing impact paper onto a board surface of the analysis board, and putting the spherical body section into pressure contact with the impact paper in a state where a reference point on the jaw model is in contact with the circular arc drawing section.

7. An articulator including a lower frame for holding a lower jaw model, an upper frame capable of holding an upper jaw model, and an occlusal plane analyzer mounted on the upper frame, wherein the occlusal plane analyzer comprises:

an analysis board made of a magnetic material;

a magnet which can be attracted to the analysis board with magnetic force, the magnet having a circular support hole going through the magnet in an attraction direction of the magnetic force; and a Monson curve imparting tool comprising a spherical body section, an extended section extending from the spherical body section, and a circular arc drawing section extending from a distal end of the extended section, the circular arc drawing section being capable of drawing a circular arc that is concentric with the spherical body section, wherein the spherical body section has a diameter that is larger than an inside diameter of the support hole and is made of a magnetic material so that the spherical body section can be attracted to the support hole by magnetic force.

\* \* \* \* \*